(12) United States Patent
Ries

(10) Patent No.: US 10,702,388 B2
(45) Date of Patent: *Jul. 7, 2020

(54) CONSTRAINED DUAL MOBILITY HIP PROSTHESIS

(71) Applicant: Howmedica Osteonics Corps, Mahwah, NJ (US)

(72) Inventor: Michael Ries, Reno, NV (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/069,365

(22) PCT Filed: Sep. 30, 2016

(86) PCT No.: PCT/US2016/054934
§ 371 (c)(1),
(2) Date: Jul. 11, 2018

(87) PCT Pub. No.: WO2017/127140
PCT Pub. Date: Jul. 27, 2017

(65) Prior Publication Data
US 2019/0029831 A1    Jan. 31, 2019

Related U.S. Application Data

(60) Provisional application No. 62/280,882, filed on Jan. 20, 2016.

(51) Int. Cl.
*A61F 2/34* (2006.01)
*A61F 2/36* (2006.01)
(Continued)

(52) U.S. Cl.
CPC .................. *A61F 2/34* (2013.01); *A61F 2/32* (2013.01); *A61F 2/3601* (2013.01);
(Continued)

(58) Field of Classification Search
CPC .... A61F 2/32; A61F 2/34; A61F 2002/30405; A61F 2002/30649; A61F 2002/30663; A61F 2002/3208; A61F 2002/3617
See application file for complete search history.

(56) References Cited

U.S. PATENT DOCUMENTS 5,624,464 A    4/1997 Wagner
7,335,231 B2    2/2008 McLean
(Continued)

FOREIGN PATENT DOCUMENTS

CA    2473074    2/2005
WO    2014124115    8/2014

OTHER PUBLICATIONS

International Search Report and Written Opinion dated Dec. 28, 2016 in Application No. PCT/US2016/054934.
(Continued)

*Primary Examiner* — Brian A Dukert
(74) *Attorney, Agent, or Firm* — Snell & Wilmer L.L.P.

(57) ABSTRACT

A system includes a constrained acetabular insert, a dual mobility liner, and a femoral head. The constrained acetabular insert has its perimeter extending beyond hemisphere and the dual mobility liner has its perimeter extending beyond hemisphere and configured to tilt and rotate within the constrained acetabular insert. The femoral head is configured to tilt and rotate within the dual mobility liner. The constrained acetabular insert may include a plurality of tabs and the dual mobility liner may include screw threads for receiving the plurality of tabs.

20 Claims, 7 Drawing Sheets

(51) Int. Cl.
*A61F 2/46* (2006.01)
*A61F 2/32* (2006.01)
*A61F 2/30* (2006.01)

(52) U.S. Cl.
CPC .......... *A61F 2/3609* (2013.01); *A61F 2/4637* (2013.01); *A61F 2002/30242* (2013.01); *A61F 2002/30245* (2013.01); *A61F 2002/30405* (2013.01); *A61F 2002/30518* (2013.01); *A61F 2002/30593* (2013.01); *A61F 2002/30594* (2013.01); *A61F 2002/30604* (2013.01); *A61F 2002/30649* (2013.01); *A61F 2002/30652* (2013.01); *A61F 2002/30663* (2013.01); *A61F 2002/3208* (2013.01); *A61F 2002/3233* (2013.01); *A61F 2002/3412* (2013.01); *A61F 2002/3443* (2013.01); *A61F 2002/3493* (2013.01)

(56) References Cited

U.S. PATENT DOCUMENTS

| | | |
|---|---|---|
| 7,520,902 B2 | 4/2009 | Deloge et al. |
| 8,608,806 B2 | 12/2013 | Harris et al. |
| 2012/0185059 A1 | 7/2012 | Vankoski et al. |

OTHER PUBLICATIONS

Non-Final Office Action issued in U.S. Appl. No. 15/282,738 dated Aug. 1, 2017.
Notice of Allowance issued in U.S. Appl. No. 15/282,738 dated Jan. 2, 2018.

CONSTRAINED DUAL MOBILITY HIP PROSTHESIS

CROSS-REFERENCE TO RELATED APPLICATIONS

This application is a U.S. national phase filing under 35 U.S.C. § 371 of PCT/US2016/054934 filed on Sep. 30, 2016, which claims priority to U.S. Provisional Application. No. 62/280,882, filed on Jan. 20, 2016, the disclosures of which are incorporated by reference in their entirety.

FIELD

The present disclosure relates to artificial implants and, more specifically, to hip or shoulder prostheses.

BACKGROUND

Whether due to degeneration, injury or otherwise, hip and shoulder joints often require replacement. Artificial implants are common in such applications. Such implants, in the hip joint context, often comprise an acetabular prosthesis and a femoral prosthesis. The acetabular prosthesis may comprise an acetabular insert or cup and a dual mobility liner.

The acetabular component typically includes a metal shell which is attached to the pelvic bone and an insert which fits inside the metal shell. A fixed bearing comprises a single mobile articulation between the femoral head and acetabular insert. The insert of a fixed bearing is typically made of an ultra-high-molecular-weight polyethylene (polymer), metal, or ceramic material into which the femoral head typically made of metal or ceramic fits into and articulates. A dual mobility component typically includes a metal insert or similar hard material into which a mobile polymer bearing liner fits into and articulates, and a metal or ceramic femoral head which fits inside and articulates with the mobile bearing liner. Movement can occur between the femoral head and inner surface of the mobile bearing liner and also between the outer surface of the mobile bearing liner and inner surface of the acetabular insert in a dual mobility bearing component. A femoral head of the femoral prosthesis is free to tilt, rotate and swivel within the dual mobility liner which is, in turn, free to tilt, rotate and swivel within the acetabular insert. That is, the dual mobility liner can be tilted, rotated and swiveled between the femoral head and the acetabular insert without affecting the position of the hip joint.

In a fixed bearing constrained acetabular component, which is intended to prevent the femoral head from separating or dislocating from the acetabular component, the liner typically extends beyond a hemisphere to contain the femoral head. In a fixed bearing constrained component with a polymer insert, the insert can expand or deform during insertion of the femoral head to allow the femoral head into the center of the insert. In a constrained acetabular insert of a dual mobility bearing in which the liner is made of a hard metal or similar material, (i.e., an acetabular insert that extends beyond hemisphere to constrain the dual mobility liner contained therein from dislocating), inserting the dual mobility liner (which also extends beyond hemisphere to constrain the femoral head contained therein from dislocating) presents challenges. The present disclosure addresses this need.

SUMMARY

In various embodiments, a system is disclosed herein that includes a constrained acetabular insert, a dual mobility liner, and a femoral head. The constrained acetabular insert has its perimeter extending beyond a hemisphere and the dual mobility liner has its perimeter extending beyond a hemisphere and is configured to tilt and rotate within the constrained acetabular insert. The femoral head is configured to tilt and rotate within the dual mobility liner. The constrained acetabular insert may include a plurality of tabs and the dual mobility liner may include screw threads for receiving the plurality of tabs.

Also disclosed herein, according to various embodiments, is a system that includes a constrained acetabular insert defining a first cavity and having a plurality of tabs. The plurality of tabs are disposed beyond the hemisphere of the constrained acetabular insert. The system also includes a dual mobility liner defining a second cavity and having an outer surface. The outer surface extends beyond the hemisphere of the dual mobility liner and includes screw threads. The dual mobility liner is configured to tilt and rotate within the first cavity. The system further includes a femoral head configured to tilt and rotate within the second cavity. The screw threads are configured to receive the plurality of tabs.

In various embodiments, a method is also disclosed herein. The method includes engaging a plurality of tabs of a constrained acetabular insert with screw threads on an outer surface of a dual mobility liner and rotating the dual mobility liner relative to the constrained acetabular insert to pass the plurality of tabs through the screw threads to insert the dual mobility liner within a cavity of the constrained acetabular insert. The dual mobility liner is configured to tilt and rotate within the constrained acetabular insert.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain the principles of the disclosure.

Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation.

For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Additionally, any reference to without contact (or similar phrases) may also include reduced contact or minimal contact.

Figure 1A:
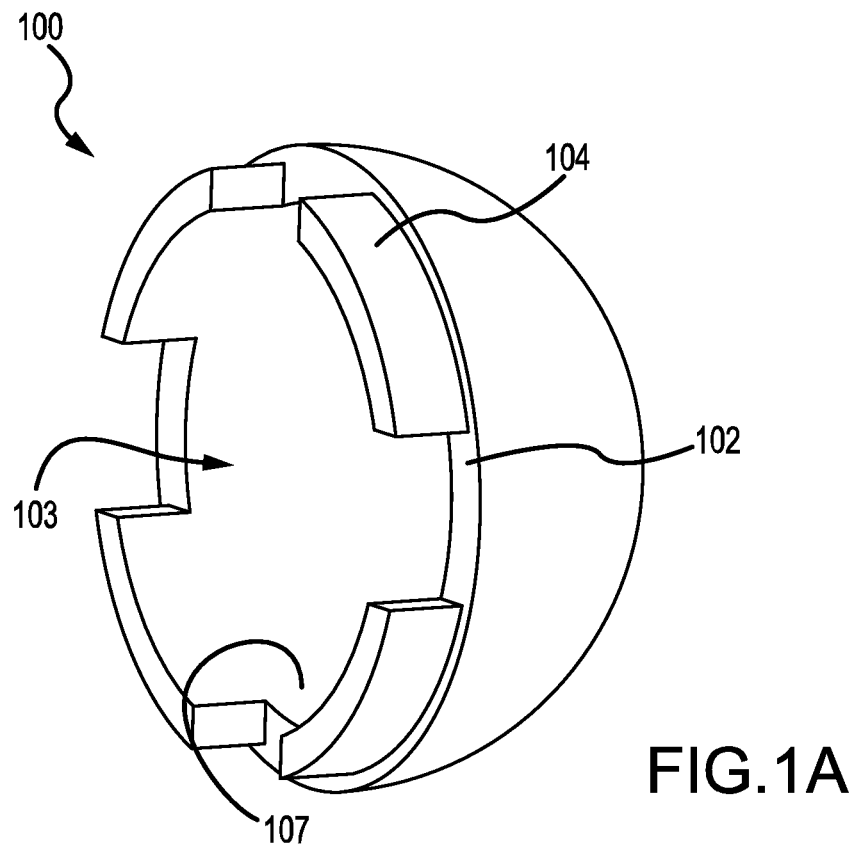
FIGS. 1A-1C illustrate perspective views of an example constrained acetabular insert and an example dual mobility liner, respectively, according to various embodiments and as disclosed herein.
Figure 1B:
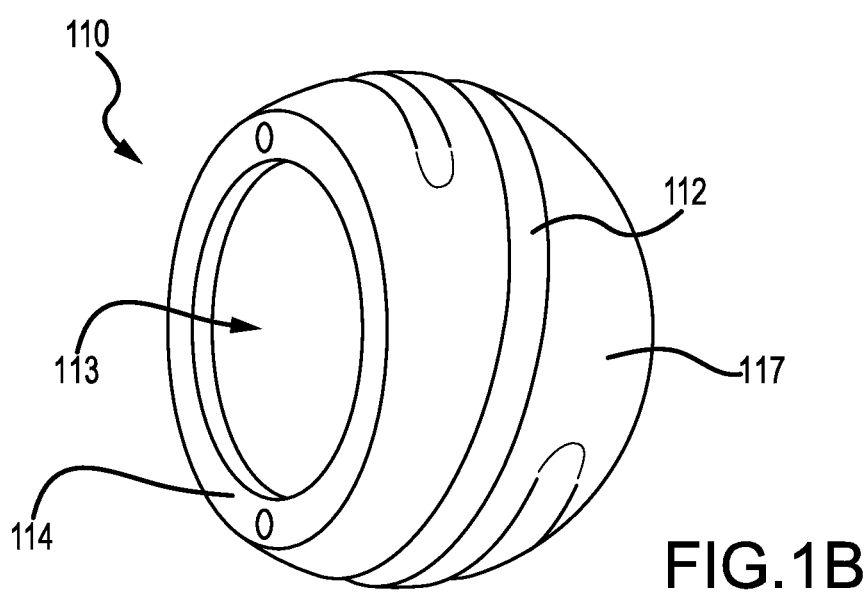

In accordance with various embodiments, and with reference to FIGS. 1A and 1B, the present disclosure includes a constrained acetabular insert or cup 100 and a dual mobility liner 110. The constrained acetabular insert 100 is configured to receive the dual mobility liner 110 and retain the dual mobility liner 110 while still allowing the dual mobility liner 110 to tilt and rotate.

In various embodiments, and with reference to FIGS. 1A-2D, the constrained acetabular insert 100 has a first cavity 105 and the dual mobility liner 110 has a second cavity 115. The first cavity 105 and/or the second cavity 115 may be spherical. That is, the first cavity 105 and/or the second cavity 115 may have a spherical shape. In various embodiments, the first cavity 105 and/or the second cavity 115 may not be a complete sphere but may be a partial sphere (i.e., may be semi-spherical). The constrained acetabular insert 100 may have a first rim 102 that defines a first opening 103 to the first cavity 105 and the dual mobility liner 110 may have a second rim 114 that defines a second opening 113 to the second cavity 115. While the maximal outer diameter of the dual mobility liner 110 may be greater than the inner diameter of the first opening 103, the dual mobility liner 110, as described in greater detail below, includes an outer surface 117 having screw threads 112 that enable the dual mobility liner 110 to be inserted into the first cavity 105 of the constrained acetabular insert 100. A femoral head 120 (FIG. 2D) may be received into the second cavity 115 of the dual mobility liner 110. Accordingly, the dual mobility liner 110 can be tilted and rotated relative to both the constrained acetabular insert 100 and the femoral head 120. The femoral head 120 is part of, or configured to be coupled to, a stem of the prosthesis that will be anchored to a patient's leg/femur.

In various embodiments, the constrained acetabular insert 100 extends beyond its hemisphere. In other words, the constrained acetabular insert 100 may comprise more than a half-sphere such that an outer diameter of the first rim 102 (or a virtual outer diameter defined by tabs extending from the first rim 102, or edge portions thereof, as discussed below) is less than a maximum outer diameter (i.e., the diameter of the hemisphere) of the constrained acetabular insert 100. Similarly, the dual mobility liner 110, according to various embodiments, extends beyond its hemisphere and thus an outer diameter of the second rim 114 is less than a maximum outer diameter (i.e., the diameter of the hemisphere) of the dual mobility liner 110.

The portion of the constrained acetabular insert 100 that extends beyond a hemisphere (which may or may not include tabs extending from the first rim 102, or edge portions thereof) is referred to herein as the constrained portion and is configured to retain the dual mobility liner 110 within the first cavity 105. That is, as mentioned above, the dual mobility liner 110 may be retained within the first cavity 105 of the constrained acetabular insert 100 while still allowing the dual mobility liner 110 to rotate and/or tilt relative to the constrained acetabular insert 100.

As mentioned above, the dual mobility liner 110 includes screw threads 112 formed on the outer surface 117, according to various embodiments. The screw threads 112 engage the constrained portion of the constrained acetabular insert 100. That is, at least edge portions of the constrained portion of the constrained acetabular insert 100 can be received into the screw threads 112, thereby allowing the dual mobility liner 110 to be threadably inserted through the first opening 103 defined by the first rim 102 and into the first cavity 105. In various embodiments, the relative rotation between the constrained acetabular insert 100 and the dual mobility liner 110, once the constrained portion is engaged with the screw threads 112, causes the constrained portion to pass entirely through the screw threads 112 as the dual mobility liner 110 passes through the first opening 103 into the first cavity 105.

In various embodiments, the screw threads 112 may extend across at least a portion of the outer surface 117 that is the hemisphere. That is, the screw threads 112 may extend across the portion of the dual mobility liner 110 having the greatest dimension. In various embodiments, the screw threads 112 may be in a single direction (e.g., clockwise or counter-clockwise). In various embodiments, the screw threads 112 may include different tracks that enable rotation in either a clockwise or a counter-clockwise direction. In various embodiments, a screw thread 112 may extend less than 360 degrees around the outer surface 117, or less than about 270 degrees, or less than about 180 degrees.

Figure 1C:
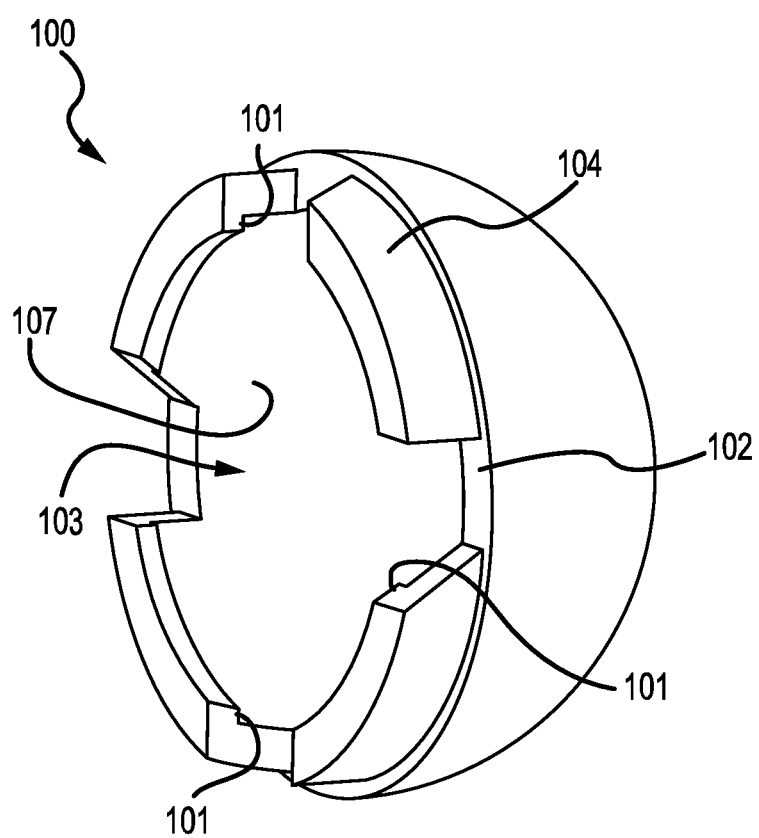

In various embodiments, the first rim 102 of the constrained acetabular insert 100 can include a plurality of tabs 104, for example, 2, 3, 4, 5, 6 or more tabs 104. In various embodiments, the first rim 102 may not have any tabs (or may have a single continuous tab). The tabs 104 may be cut into or extend from the rim 102. In various embodiments, the tabs 104 are circumferentially spaced apart from each other. According to various embodiments, each tab of the plurality of tabs 104, or at least an edge portion of the tabs 104 or an inner diameter thereof, may engage and be received within the screw threads 112 of the dual mobility liner 110. In various embodiments, at least the portion of each tab 104 that extends beyond the hemisphere of the constrained acetabular insert 100 engages with the screw threads 112 of the dual mobility liner 110. For example, the portion of each tab 104 that extends beyond the hemisphere of constrained acetabular insert 100 forms a skirt that can be received within screw threads 112. In this regard, the inner diameter of tabs 104 can form a virtual radius so dual mobility liner 110 can freely rotate within constrained acetabular insert 100. With reference to FIG. 1C, and according to various embodiments, each tab 104 can comprise a lip 101 or step or that engages with screw threads 112 of dual mobility liner 110. In various embodiments, each tab 104 comprises a rectangular cross section, yet other cross sections are contemplated, including cross sections that facilitate entry of tabs 104 into screw threads 112, for example, a trapezoidal or other non-rectangular cross section as shown in FIG. 1C.

In various embodiments, the shape and dimensions of an inner surface 107 of the first cavity 105 may complement and correspond with the shape and dimensions of an outer surface 117 of the dual mobility liner 110. That is, the dual mobility liner 110 may be configured to nest within the first cavity 105 of the constrained acetabular insert 100 such that the respective surfaces 107, 117 (FIGS. 2B and 2C) complementarily engage (i.e., "match") each other. For example, the outer surface 117 of the dual mobility liner 110 may be, except for the screw threads, continuously spherical and may be dimensioned to nest against a complementary and continuously spherical inner surface 107 of the first cavity 105 of the constrained acetabular insert 100. That is, the outer surface 117 of the dual mobility liner 110, with the exception of the first opening 103 defined by the first rim 102 and the screw threads 112, may have a continuously spherical shape and thus may be free of corners and/or edges.

In various embodiments, the outer surface 117 of the dual mobility liner 110 may be free of planar surfaces. In other words, except for the screw threads 112 on the outer surface 117 and the second opening 113 defined by the second rim 114, the dual mobility liner 110 is a sphere or semi-sphere. In various embodiments, when the dual mobility liner 110 is within the first cavity 105 and when the first opening 103 is parallel to the second opening 113, there are no voluminous gaps between the outer surface 117 of the dual mobility liner 110 and the inner surface 107 of the first cavity 105. Said differently, all of the surface area of the outer surface 117 of the dual mobility liner 110, with the sole exception being the screw threads 112, is available to engage the inner surface 107 of the constrained acetabular insert 100, thereby increasing the strength of the prosthesis.

In accordance with example embodiments shown in FIGS. 2A-2D, and as described above, the dual mobility liner 110 can be reduced into the constrained acetabular insert 100 by rotating the dual mobility liner 110 in a first direction (e.g., clockwise or counter-clockwise) in relation to the constrained acetabular insert 100.

Figure 2A:
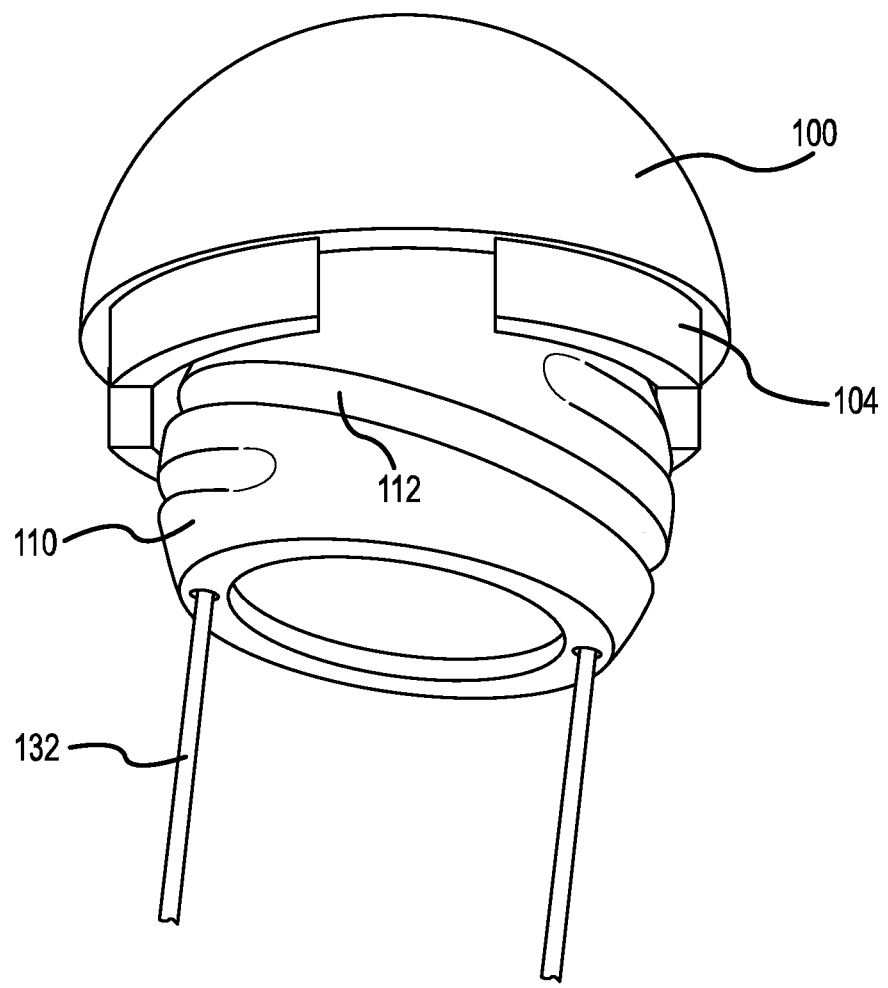
FIGS. 2A-2D illustrate perspective and cross-sectional views of constrained acetabular inserts being screw-threaded with dual mobility liners, according to various embodiments and as disclosed herein.
Figure 2B:
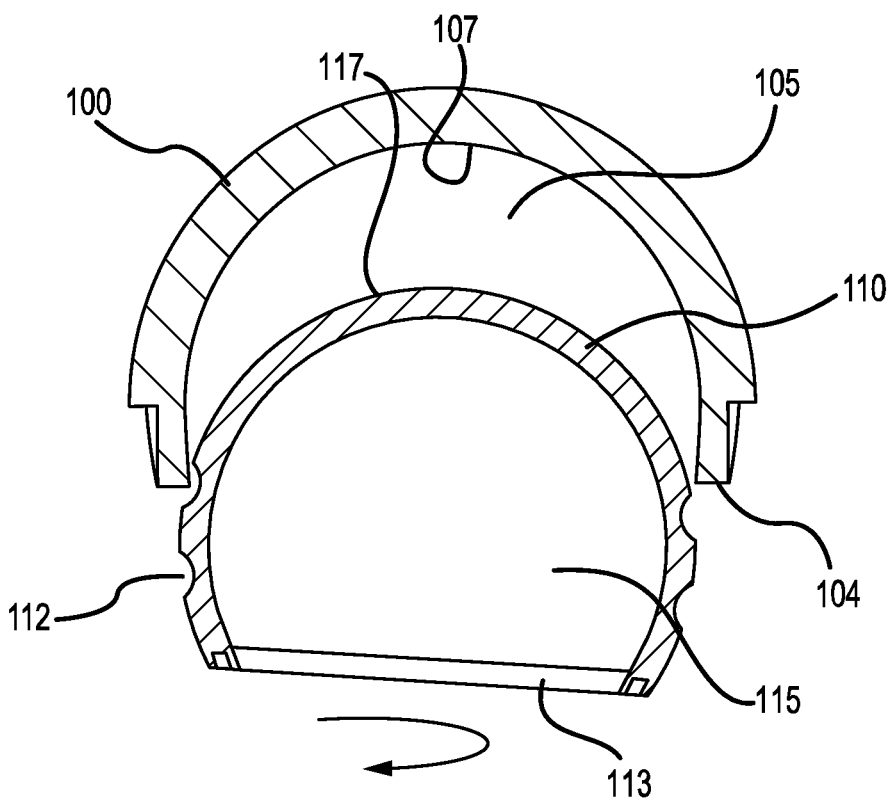
Figure 2C:
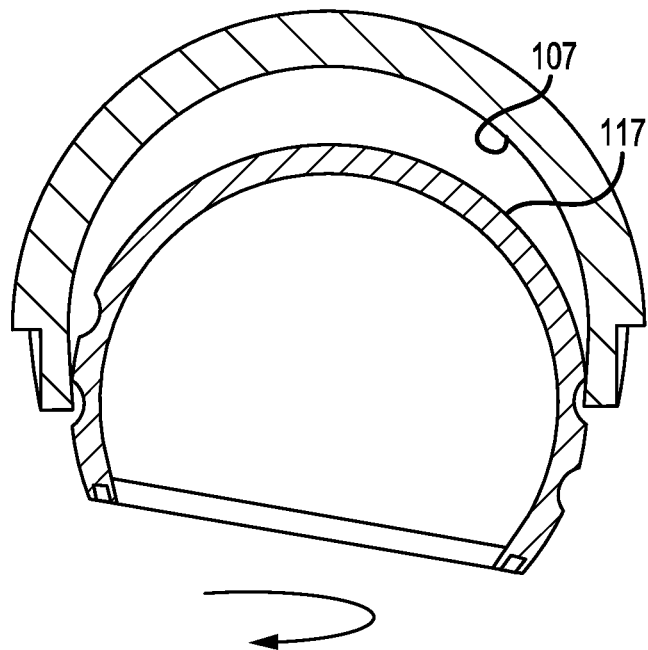
Figure 2D:
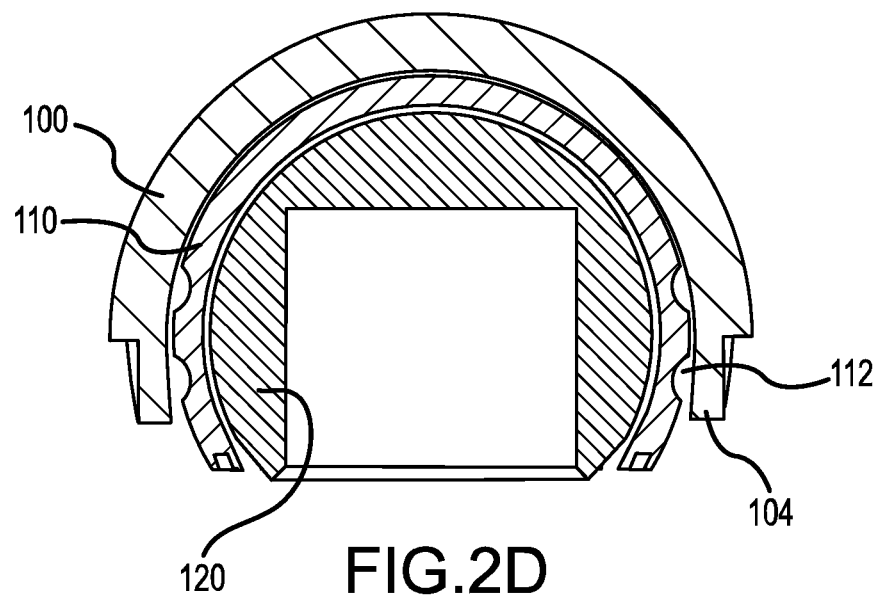
Figure 3:
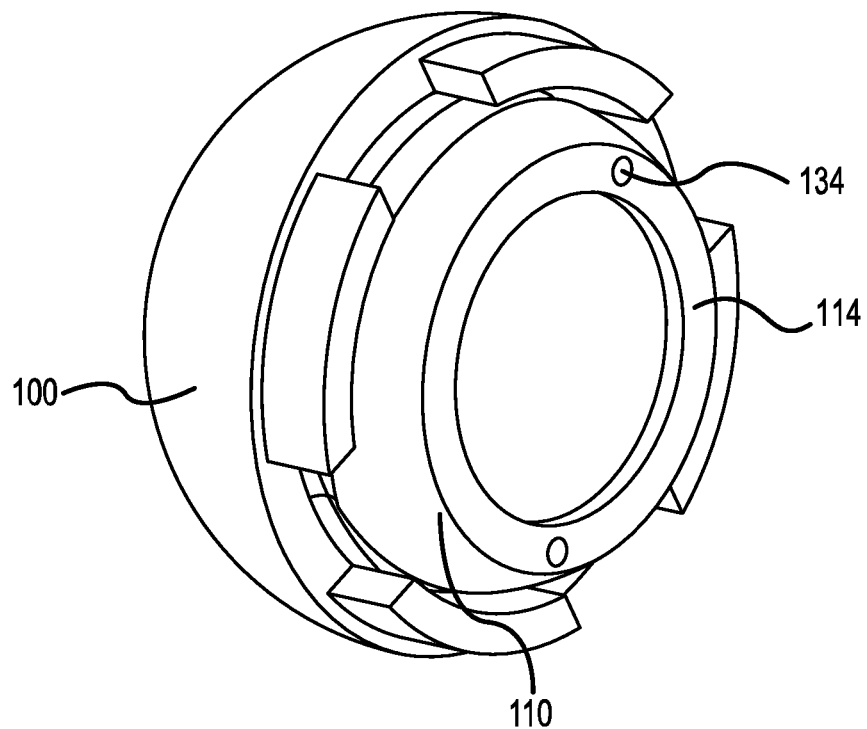
FIG. 3 illustrates a perspective view of an example dual mobility liner contained within an example constrained acetabular insert, according to various embodiments and as disclosed herein.

In accordance with example embodiments, the plurality of tabs 104 of the constrained acetabular insert 100 engage the screw threads 112 of the dual mobility liner 110 until, with reference to FIGS. 2D and 3, the screw threads 112 are past the tabs 104 and the dual mobility liner 110 is fully contained within the constrained acetabular insert 100, thereby enabling the dual mobility liner 110 to tilt, rotate and swivel within the constrained acetabular insert 100. In this regard, various embodiments of the present disclosure do not require tilting of the dual mobility liner 110 with respect to the constrained acetabular insert 100 for it to receive the dual mobility liner 110.

Various embodiments of the present disclosure do not require removing as much of the dual mobility liner bearing surface as in the prior art. Put another way, the present disclosure retains a larger portion of the dual mobility liner bearing surface (e.g., only the screw thread(s) is/are removed from the dual mobility liner bearing surface) which maintains greater surface area of contact (this reduces contact stresses and wear at the bearing surface), provides greater range of motion in comparison to the prior art, and provides increased stability (e.g., more difficult to dislocate in comparison to the prior art).

In accordance with example embodiments, removing dual mobility liner 110 from constrained acetabular insert 100 can be accomplished by aligning tabs 104 with screw threads 112 and rotating in a second direction opposite the first direction (e.g., counter-clockwise or clockwise).

Figure 4:
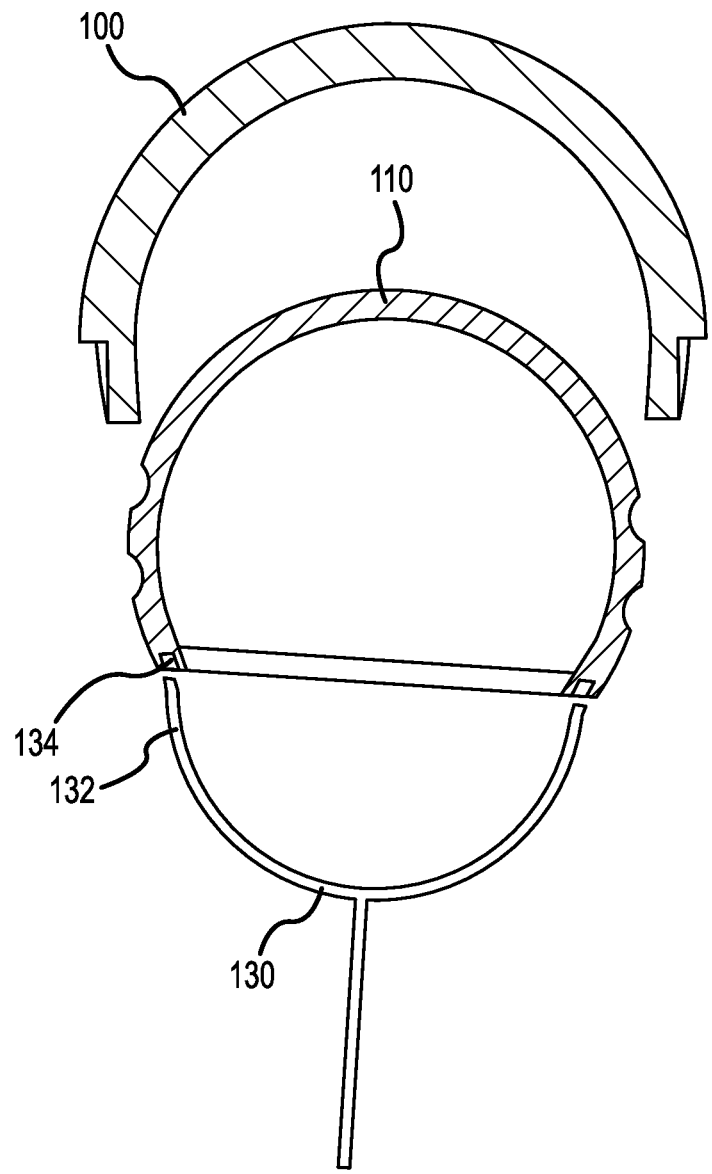
FIG. 4 illustrates a rotation instrument in accordance with an example embodiment of the present disclosure.

In various embodiments, and with reference to FIG. 4 (and FIGS. 2A and 3), dual mobility liner 110 can be screw threaded with respect to constrained acetabular insert 100 with a rotation instrument 130. By way of example, one or more features 132 of rotation instrument 130 can engage with one or more engagement features/recesses 134 or the like within a wall of, or otherwise on, dual mobility liner 110.

In accordance with example embodiments, a constrained acetabular insert, dual mobility liner and rotation instrument of the present disclosure can be comprised in a kit.

The constrained acetabular insert may be a shell that is attached to the pelvic bone. The shell-like constrained acetabular insert may be made from a metallic material, a polymeric material, or ceramic material, among others. The dual mobility liner may be made from a metallic material, a polymeric material, or a ceramic material, among others. Articulation and/or movement can occur between the femoral head and the inner surface of the dual mobility liner and also between the outer surface of the dual mobility liner and inner surface of the constrained acetabular insert, as mentioned above.

Figure 5:
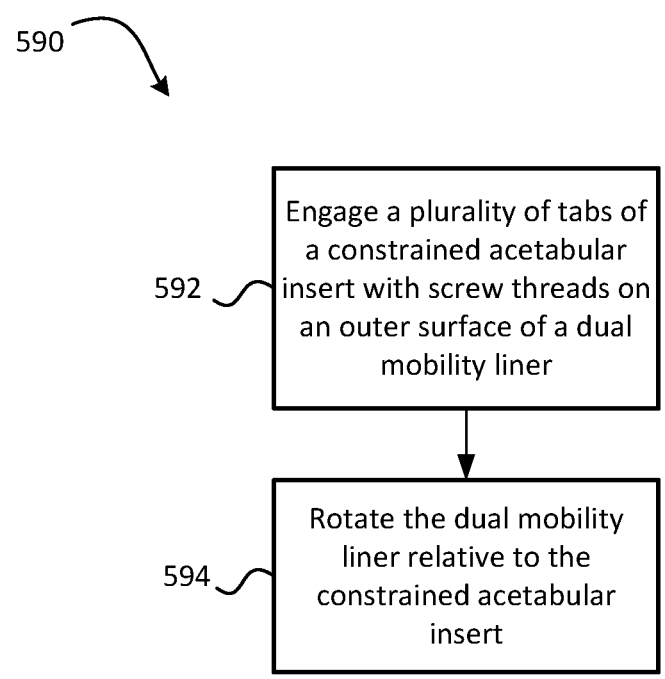
FIG. 5 illustrates a schematic flow chart diagram of a method of using a constrained acetabular insert and a dual mobility liner, in accordance with various embodiments.

Methods of use of the constrained acetabular insert, dual mobility liner and rotation instrument disclosed herein are also within the scope of the present disclosure. For example, FIG. 5 is a schematic flow chart diagram of a method 590 of using the prosthesis disclosed herein. More specifically, the method 590 may include engaging the plurality of tabs 104 of the constrained acetabular insert 100 with screw threads 112 on the outer surface 117 of the dual mobility liner 110 at step 592. The method 590 may further include rotating the dual mobility liner 110 relative to the constrained acetabular insert 100 to pass the plurality of tabs 140 through the screw threads 112 to insert the dual mobility liner 110 within the first cavity 105 of the constrained acetabular insert 100 at step 594. As mentioned above, the dual mobility liner 110 may be configured to tilt, rotate, and swivel within the first cavity 105 constrained acetabular insert 100.

In various embodiments, the method 590 may further include coupling the femoral head 120 within the second cavity 115 of the dual mobility liner 110 to enable the femoral head 120 to tilt, rotate, and swivel within the dual mobility liner 110. In various embodiments, the step of coupling the femoral head 120 within the second cavity 115 of the dual mobility liner 110 occurs before step 594 of rotating the dual mobility liner 110 relative to the constrained acetabular insert 100. In other words, the femoral head 120 and/or a stem of the prosthesis that will be anchored to a patient's leg may already be rotatably retained within the second cavity 115 before inserting the dual mobility liner 110 into the constrained acetabular insert 100.

In various embodiments, the femoral head 120 may be inserted into the dual mobility liner 110 before an operation or on a 'back table' of an operating room. In various embodiments, the dual mobility liner 110 may be made from a material, such as a polymeric material, that is resiliently deformable. For example, the second rim 114 of the dual mobility liner 110 may slightly expand/deform in response to the femoral had 120 being pressed/inserted through the second opening 113 and into the second cavity 115 of the dual mobility liner 110. With the femoral head 120 already being inserted into the dual mobility liner 110, the femoral head may be attached to a femur (either directly or indirectly via a femoral component/stem), according to various embodiments. The hip may then be "reduced" by screwing the dual mobility liner 110 into the constrained acetabular insert 100, which is attached to pelvic bone. In various embodiments, the femoral head 120 may be prevented from becoming dislocated from the dual mobility liner 110 because of the constrained configuration of the constrained acetabular insert 100. In other words, the constrained acetabular insert 100 may be made from a rigid (or substantially rigid) material, thereby preventing the second rim 114 of the dual mobility liner 110 from expanding.

In various embodiments, the constrained acetabular insert, dual mobility liner and femoral head can be comprised of the same or different materials, e.g., a cobalt-chromium alloy, oxidized zirconium, polyethylene or other polymeric materials, a ceramic, stainless steel and the like. In various embodiments, a variety of materials may be used.

It will be apparent to those skilled in the art that various modifications and variations can be made in the present disclosure without departing from the spirit or scope of the disclosure. For example, while the present disclosure has been described primarily with reference to hip joints, those skilled in the art will understand that the disclosure may be applied to shoulder joints. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

I claim:

1. A system comprising:
a constrained acetabular insert;
a dual mobility liner; and
a femoral head configured to tilt and rotate within the dual mobility liner;
wherein the constrained acetabular insert comprises at least one tab having an edge portion;
wherein the dual mobility liner comprises screw threads for receiving the edge portion of the at least one tab; and
wherein when the screw threads are received entirely past the edge portion of the at least one tab, the dual mobility liner is free to tilt within the constrained acetabular insert.

2. The system of claim 1, wherein an outer surface of the dual mobility liner is, except for the screw threads, continuously spherical.

3. The system of claim 2, wherein the screw threads extend across a hemisphere of the dual mobility liner.

4. The system of claim 1, wherein the at least one tab of the constrained acetabular insert extends from a rim of an opening of the constrained acetabular insert.

5. The system of claim 1, comprising a plurality of tabs circumferentially spaced apart from each other.

6. The system of claim 1, further comprising a rotation instrument configured to facilitate rotation of the dual mobility liner relative to the constrained acetabular insert.

7. The system of claim 6, wherein the dual mobility liner comprises an engagement feature configured to couple with the rotation instrument.

8. The system of claim 7, wherein the engagement feature comprises a recess for receiving a portion of the rotation instrument.

9. A system comprising:
a constrained acetabular insert defining a first cavity and comprising at least one tab having an edge portion;
a dual mobility liner defining a second cavity and comprising an outer surface, wherein the outer surface comprises screw threads; and
a femoral head configured to tilt and rotate within the second cavity;
wherein the screw threads are configured to receive the edge portion of the at least one tab; and
wherein when the dual mobility liner is fully contained within the constrained acetabular insert, the dual mobility liner is able to tilt and rotate within the first cavity.

10. The system of claim 9, wherein the dual mobility liner comprises an engagement feature configured to couple with a rotation instrument.

11. The system of claim 9, wherein the screw threads extend across a hemisphere of the dual mobility liner.

12. The system of claim 9, wherein the constrained acetabular insert comprises a first rim that defines a first opening to the first cavity.

13. The system of claim 12, wherein the at least one tab extends from the first rim.

14. The system of claim 9, comprising a plurality of tabs circumferentially spaced apart from each other.

15. The system of claim 12, wherein the dual mobility liner comprises a second rim that defines a second opening to the second cavity.

16. The system of claim 15, wherein with the dual mobility liner within the first cavity and with the first opening being parallel to the second opening, a portion of the outer surface of the dual mobility liner disposed within the first cavity is continuously spherical, except for the screw threads, and thus nests within an inner surface of the first cavity.

17. The system of claim 15, wherein the outer surface of the dual mobility liner is continuously spherical, except for the screw threads, and thus is free of planar surfaces.

18. A method comprising:
engaging an edge portion of at least one tab of a constrained acetabular insert with screw threads on an outer surface of a dual mobility liner; and
rotating the dual mobility liner relative to the constrained acetabular insert to pass the edge portion of the at least one tab entirely through the screw threads to insert the dual mobility liner within a cavity of the constrained acetabular insert, wherein once the edge portion of the at least one tab has been passed fully beyond the screw threads the dual mobility liner is configured to tilt and rotate within the constrained acetabular insert.

19. The method of claim 18, wherein the cavity of the constrained acetabular insert is a first cavity, the method further comprising coupling a femoral head within a second cavity of the dual mobility liner, wherein the femoral head is configured to tilt and rotate within the dual mobility liner.

20. The method of claim 19, wherein coupling the femoral head within the second cavity of the dual mobility liner occurs before rotating the dual mobility liner relative to the constrained acetabular insert.

\* \* \* \* \*